US012702348B2

(12) United States Patent
Berechet et al.

(10) Patent No.: US 12,702,348 B2
(45) Date of Patent: Aug. 11, 2026

(54) METHOD AND SYSTEM FOR CHARACTERIZING PIGMENTARY DISORDERS IN AN INDIVIDUAL

(71) Applicants: THALES, Courbevoie (FR); SISPIA, Vincennes (FR)

(72) Inventors: Ion Berechet, Vincennes (FR); Gérard Berginc, Elancourt (FR); Stefan Berechet, Joinville Le Pont (FR)

(73) Assignees: THALES, Courbevoie (FR); SISPIA, Vincennes (FR)

(*) Notice: Subject to any disclaimer, the term of this patent is extended or adjusted under 35 U.S.C. 154(b) by 847 days.

(21) Appl. No.: 17/413,506

(22) PCT Filed: Dec. 13, 2019

(86) PCT No.: PCT/EP2019/085162

§ 371 (c)(1), (2) Date: Jun. 11, 2021

(87) PCT Pub. No.: WO2020/126932

PCT Pub. Date: Jun. 25, 2020

(65) Prior Publication Data

US 2022/0071553 A1 Mar. 10, 2022

(30) Foreign Application Priority Data

Dec. 20, 2018 (FR) ...................................... 1873482

(51) Int. Cl.

*A61B 5/00* (2006.01)
*A61B 5/103* (2006.01)
(Continued)

(52) U.S. Cl.

CPC ............ *A61B 5/444* (2013.01); *A61B 5/0073* (2013.01); *A61B 5/1032* (2013.01);
(Continued)

(58) Field of Classification Search

CPC ..... A61B 5/444; A61B 5/0073; A61B 5/1032; G06T 7/90; G06T 7/0012;
(Continued)

(56) References Cited

U.S. PATENT DOCUMENTS 8,836,762 B2 * 9/2014 Berginc ................ G06T 11/006 235/404
8,837,796 B1 * 9/2014 Zalutskaya ............... G06T 5/92 128/923

(Continued)

FOREIGN PATENT DOCUMENTS

JP 2009-504272 A 2/2009

OTHER PUBLICATIONS

Korotkov, et al., "Computerized analysis of pigmented skin lesions: A review", Artificial Intelligence in Medicine, vol. 56, Issue 2, pp. 69-90, Oct. 2012.

(Continued)

*Primary Examiner* — Justin Xu
*Assistant Examiner* — Jonathan M Haney
(74) *Attorney, Agent, or Firm* — BakerHostetler

(57) ABSTRACT

A method for characterizing cutaneous pigmentary disorders in an individual which includes: for each pigmentary disorder: on a date tkm acquiring 2D images of a pigmentary disorder from a plurality of angles and reconstructing at least one 3D image; storing the images in a first folder; on the basis of the images, calculating parameters of the pigmentary disorder, and storing in a second folder; evaluating the parameters and storing in a third folder; iterating at least one of the four preceding steps on multiple dates, and for each iteration: comparing the data for at least one period and identifying the changes; storing in a fourth folder per period; for each fourth folder, grouping the folders together in a fifth folder defining a snapshot of the pigmentary disorder; aggre- (Continued)

gating the fifth folders in a sixth folder defining a dynamic profile of the pigmentary disorder; iterating the preceding steps to obtain a sixth folder for each additional pigmentary disorder; and generating, for the individual, a knowledge base of their pigmentary disorders aggregating the sixth folders.

15 Claims, 9 Drawing Sheets

(51) Int. Cl.
*G06T 7/00* (2017.01)
*G06T 7/90* (2017.01)
*G16H 30/20* (2018.01)

(52) U.S. Cl.
CPC .............. *G06T 7/0012* (2013.01); *G06T 7/90* (2017.01); *G16H 30/20* (2018.01); *G06T 2207/10072* (2013.01); *G06T 2207/30088* (2013.01)

(58) Field of Classification Search
CPC ........... G06T 2207/10072; G06T 2207/30088; G16H 30/20
See application file for complete search history.

(56) References Cited

U.S. PATENT DOCUMENTS

| | | | | |
|---|---|---|---|---|
| 2009/0118600 | A1 | 5/2009 | Ortiz et al. | |
| 2011/0270200 | A1 | 11/2011 | Edgar et al. | |
| 2011/0273535 | A1 | 11/2011 | Mendelson | |
| 2016/0256098 | A1* | 9/2016 | Grochowina | A61B 5/0013 |
| 2017/0345204 | A1* | 11/2017 | Berechet | G06T 7/136 |
| 2018/0146912 | A1* | 5/2018 | Rundo | A61B 5/444 |
| 2018/0206780 | A1* | 7/2018 | Pyun | A61B 5/444 |
| 2019/0166312 | A1* | 5/2019 | Tashayyod | H04N 23/951 |

OTHER PUBLICATIONS

Wazaefi, et al., "Evidence of a Limited Infra-Individual Diversity of Nevi: Intuitive Perception of Dominant Clusters Is a Crucial Step in the Analysis of Nevi by Dermatologists", The Society for Investigative Dermatology, pp. 2355-2361, Apr. 2013.

Oreno, et al., "Algorithm for dermocosmetic use in the management of cutaneous sideeffects associated with targeted therapy in oncology", Journal of the European Academy of Dermatology and Venereology, pp. 1071-1080, Feb. 2013.

* cited by examiner

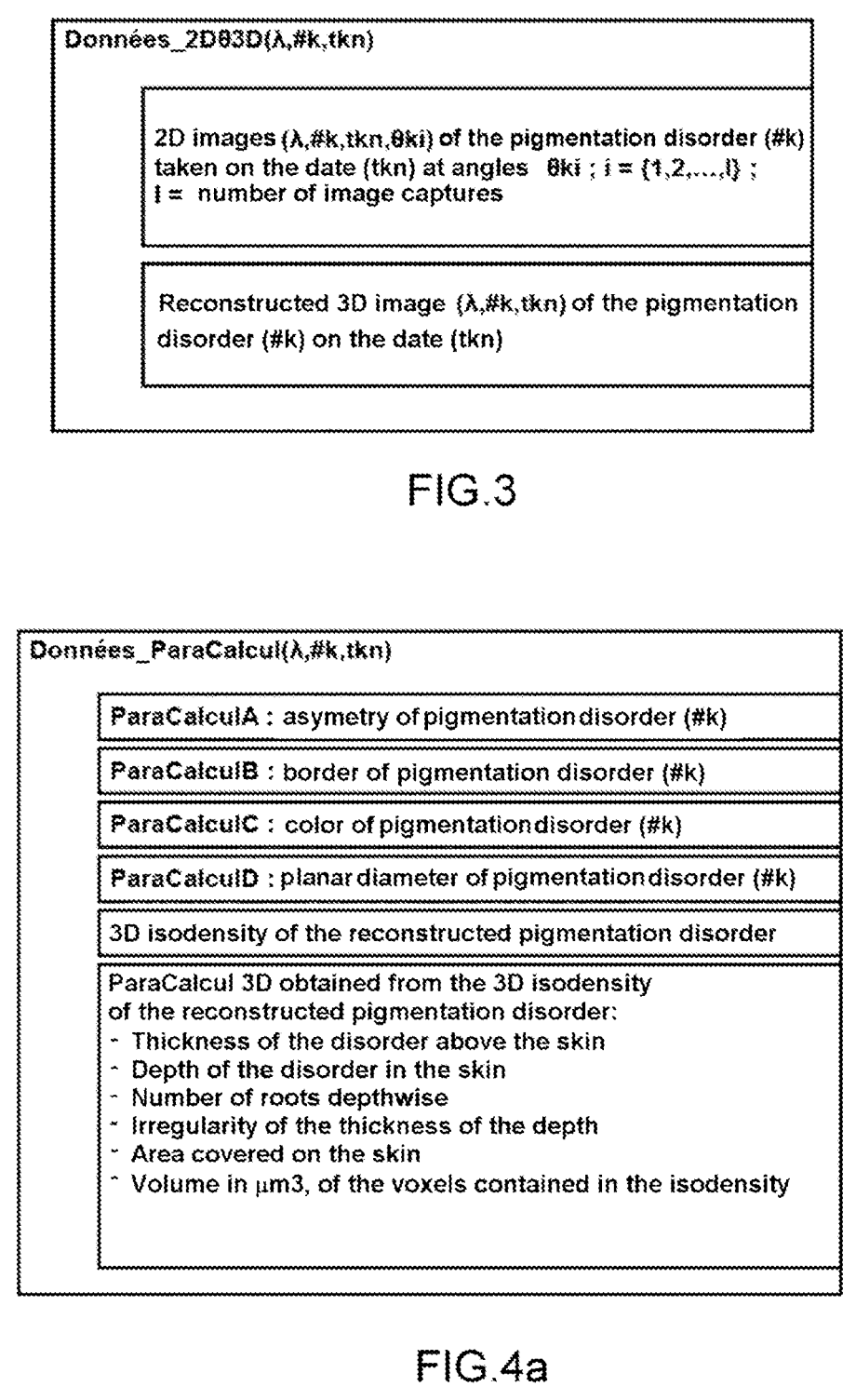

Données_2D83D(λ,#k,tkn)

2D images (λ,#k,tkn,θki) of the pigmentation disorder (#k) taken on the date (tkn) at angles θki ; i = {1,2,...,I} ; I = number of image captures Reconstructed 3D image (λ,#k,tkn) of the pigmentation disorder (#k) on the date (tkn)

FIG.3

Données_ParaCalcul(λ,#k,tkn)

ParaCalculA : asymetry of pigmentation disorder (#k)

ParaCalculB : border of pigmentation disorder (#k)

ParaCalculC : color of pigmentation disorder (#k)

ParaCalculD : planar diameter of pigmentation disorder (#k)

3D isodensity of the reconstructed pigmentation disorder

ParaCalcul 3D obtained from the 3D isodensity of the reconstructed pigmentation disorder:

- Thickness of the disorder above the skin
- Depth of the disorder in the skin
- Number of roots depthwise
- Irregularity of the thickness of the depth
- Area covered on the skin
- Volume in μm3, of the voxels contained in the isodensity

FIG.4a

Données_ParaExpertMétier(λ,#k,tkn)

ABCD criteria evaluated by the expert for the pigmentation disorder (#k) on the date (tkn)

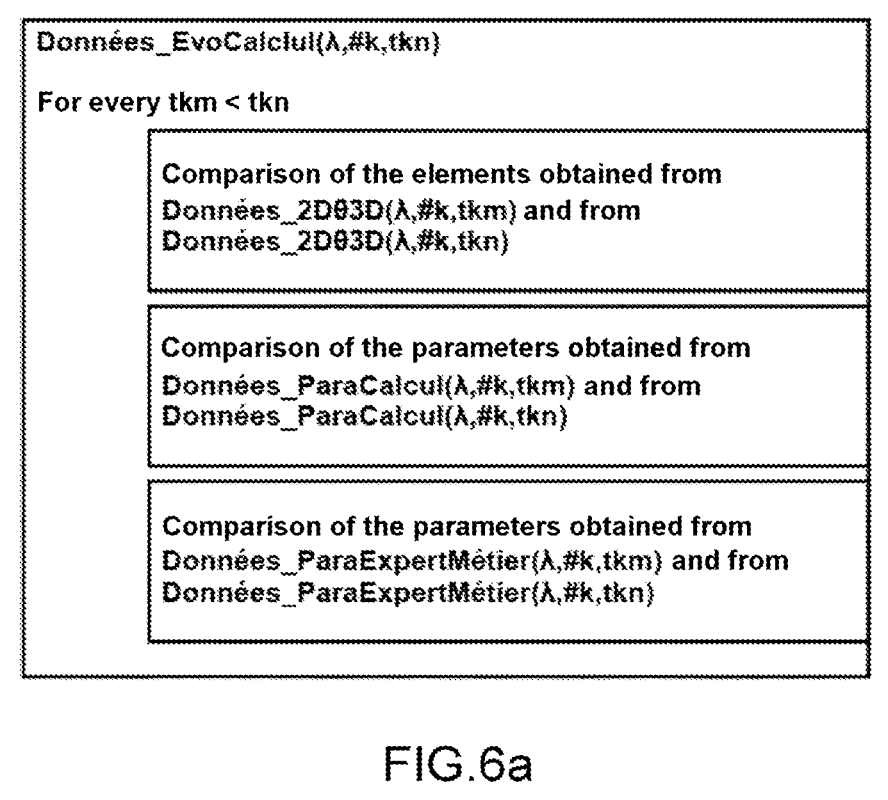

Données_EvoCalclul(λ,#k,tkn)

For every tkm < tkn

Comparison of the elements obtained from
Données_2Dθ3D(λ,#k,tkm) and from
Données_2Dθ3D(λ,#k,tkn)

Comparison of the parameters obtained from
Données_ParaCalcul(λ,#k,tkm) and from
Données_ParaCalcul(λ,#k,tkn)

Comparison of the parameters obtained from
Données_ParaExpertMétier(λ,#k,tkm) and from
Données_ParaExpertMétier(λ,#k,tkn)

FIG.6a

PDDP(λ,#k)
Dynamic profile of the pigmentation disorder (#k) of the individual (λ)

IDDP(λ,#k,tk0)
Snapshot of the pigmentation disorder (#k) on the date (tk0)

IDDP(λ,#k,tk1)
Snapshot of the pigmentation disorder (#k) on the date (tk1)

...

IDDP(λ,#k,tkn)
Snapshot of the pigmentation disorder (#k) on the date (tkn)

BCGDP

BCDP(λ1)

PDDP(λ1,#11) PDDP(λ1,#12) ... PDDP(λ1,#1k

BCDP(λ2)

PDDP(λ2,#21) PDDP(λ2,#22) ... PDDP(λ2,#2k

...

... ... ...

BCDP(λp)

PDDP(λp,#p1) PDDP(λp,#p2) ... PDDP(λp,#pk

FIG.9

METHOD AND SYSTEM FOR CHARACTERIZING PIGMENTARY DISORDERS IN AN INDIVIDUAL

CROSS-REFERENCE TO RELATED APPLICATIONS

This application is a National Stage of International patent application PCT/EP2019/085162, filed on Dec. 13, 2019, which claims priority to foreign French patent application No. FR 1873482, filed on Dec. 20, 2018, the disclosures of which are incorporated by reference in their entirety.

FIELD OF THE INVENTION

The invention relates to a method and system for characterizing in two-dimensions (2D) and three-dimensions (3D) and evaluating the external and internal progression of skin pigmentation disorders.

BACKGROUND

To evaluate pigmentation disorders of the skin (moles, benign lesions, malignant lesions, carcinomas, melanomas, etc.), dermatological techniques are based on criteria called ABCD. Thus, a pigmentation disorder is characterized by:

its asymmetry (A), its border (B), its color (C), its diameter (D).

In addition, dermatologists attempt to assess the non-uniformity of the thickness of the pigment disorder using two-dimensional imaging techniques in the field of visible imaging.

The challenge for dermatologists is to identify suspicious "moles" as early as possible and to develop a new semiology.

A few research centers and hospitals have joined forces, mainly in Australia, USA and Germany, to construct a larger database and to take an additional step in the classification of pigmentary patches with expert systems. Despite encouraging results, this approach suffers from an acquisition limited to an often uncalibrated two-dimensional color image, everything about which leads it to be believed that it will remain insufficient in terms of specificity and sensitivity.

Models for predictive evaluation of the behavior of pigmentation disorders (such as described for example in the publications by Yanal Wazaefi, Caroline Marqueste, Giovanni Pellacani, Luc Thomas, "Evidence of a Limited Infra-Individual Diversity of Nevi: Intuitive Perception of Dominant Clusters Is a Crucial Step in the Analysis of Nevi by Dermatologists", Journal of Investigative Dermatology, April 2013, or by Rene-Jean Bensadoun, Jean Krutmann, Philippe G Humbert, Thomas Luger, "Algorithm for dermocosmetic use in the management of cutaneous side effects associated with targeted therapy in oncology", Journal of the European Academy of Dermatology and Venereology, February 2013) of the behavior of pigmentation disorders are limited to two-dimensional parameters and do not incorporate dimensions reflecting the depth, volume, thickness and surface roughness of the pigmentation disorder requiring precise three-dimensional imaging allowing a predictive analysis.

SUMMARY OF THE INVENTION

The aim of the invention is to alleviate these drawbacks.

More precisely, the subject of the invention is a method for characterizing skin pigmentation disorders of an individual, which comprises:

- for each pigmentation disorder:
  - on a date tkm
    - acquiring 2D images of a pigmentation disorder from a plurality of angles and reconstructing at least one 3D image,
    - storing said images in a first folder,
    - from said images, computing parameters of the pigmentation disorder, and storing in a second folder,
    - evaluating said parameters and storing in a third folder,
  - iterating at least one of the previous four steps on a plurality of dates, and for each iteration:
    - comparing data in at least one period and identifying changes,
    - storing in one fourth folder per period,
    - for each fourth folder, grouping folders in a fifth folder defining a snapshot of the pigmentation disorder,
    - aggregating the fifth folders into a sixth folder defining a dynamic profile of the pigmentation disorder,
- iterating the previous steps to obtain a sixth folder for each other pigmentation disorder, and
- generating, for the individual, a knowledge base of his or her pigmentation disorders aggregating the sixth folders.

The method according to the invention makes it possible to generate, for an individual λ, a knowledge base BCDP(λ) of his or her pigmentation disorders containing a plurality of data fields.

Another subject of the invention is a system for characterizing skin pigmentation disorders of an individual, comprising a processor programmed to implement the following steps:

- for each pigmentation disorder:
  - on a date tkm
    - acquiring 2D images of a pigmentation disorder on a date tkm and from a plurality of viewing angles and reconstructing at least one 3D image from said processed 2D images and
    - storing said 2D and 3D images in a first folder associated with the individual, with the pigmentation disorder and with tkm,
    - from said 2D and 3D images, computing predefined parameters of the pigmentation disorder via first computing means of the system, and storing said parameters in a second folder associated with the individual, with the pigmentation disorder and with tkm,
    - acquiring an evaluation of said parameters and storing said evaluation in a third folder associated with the individual, with the pigmentation disorder and with tkn,
  - iterating at least one of the previous four steps on a plurality of dates tkm up to tkn (tkn>tkm), and for each iteration:
    - comparing the data of the first, second and third folders in at least one period between the dates tkn and tkm and identifying changes in said data with second computing means of the system, storing the changes in at least one fourth folder, associated with the individual, with the pigmentation disorder and with tkn, with one fourth folder per period, for each fourth folder, grouping the first, second, third and fourth folders associated with tkn into a fifth folder with the individual, with the pigmentation disorder and with tkn, defining a snapshot of the pigmentation disorder, aggregating the fifth folders into a sixth folder with the individual and with the pigmentation disorder, defining a dynamic profile of the pigmentation disorder, iterating the previous steps to obtain a sixth folder for each other pigmentation disorder of the individual, and generating, for the individual, a knowledge base of his or her pigmentation disorders aggregating the sixth folders.

BRIEF DESCRIPTION OF THE DRAWINGS

Other features and advantages of the invention will become apparent on reading the following detailed description, which is given by way of non-limiting example and with reference to the appended drawings, in which:

FIG. 9 is a schematic representation of (BCGDP)—a global knowledge base of pigmentation disorders (BCGDP being the acronym of the French expression Base de Connaissances Globale des Désordres Pigmentaires [global knowledge base of pigmentation disorders]).

In all the figures, elements that are the same have been designated with the same references.

DETAILED DESCRIPTION

Figure 1A:
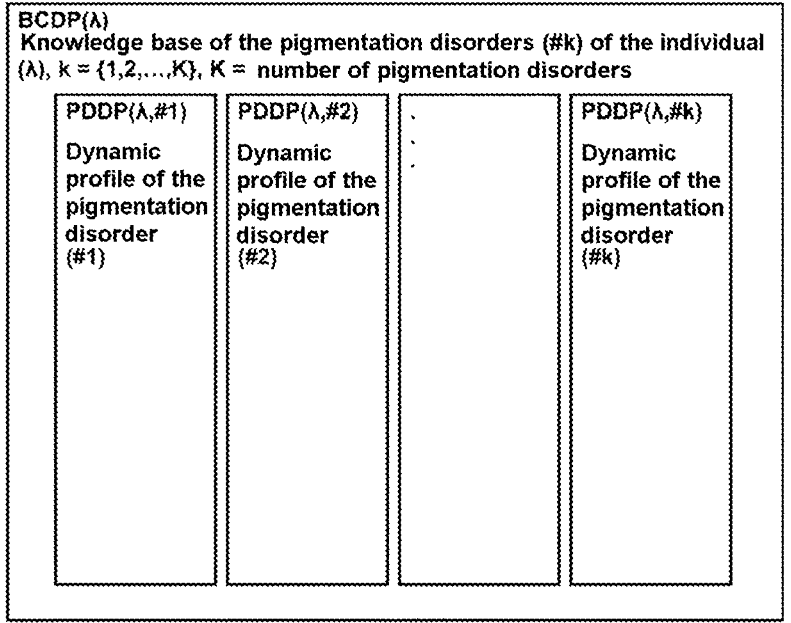
FIG. 1*a* is a schematic representation of the content of the knowledge base BCDP(λ) of the pigmentation disorders of the individual λ.
Figure 1B:
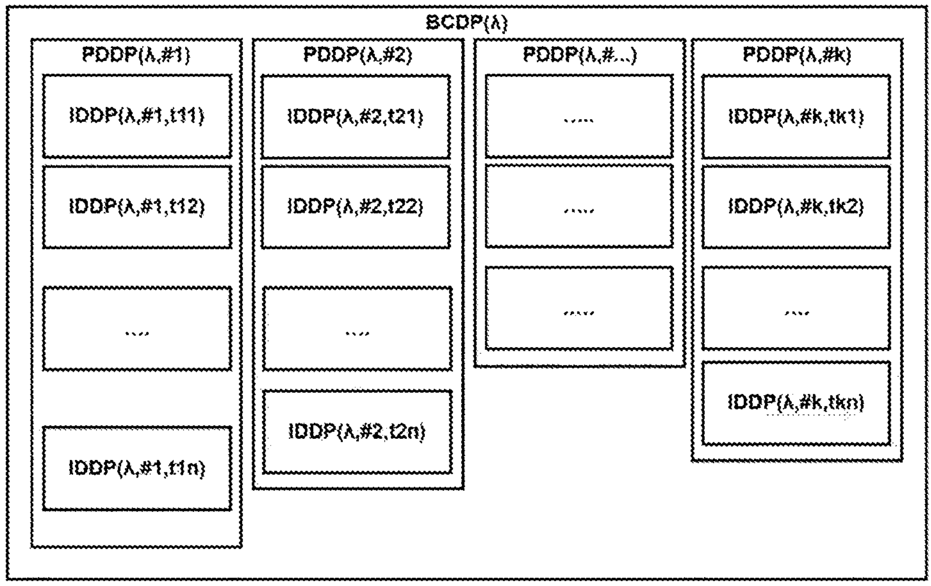
FIG. 1*b* is a more detailed schematic representation.

The method according to the invention makes it possible to generate, for an individual λ, a knowledge base BCDP(λ) of his or her pigmentation disorders, this base containing a plurality of data fields, as shown in FIGS. 1*a* and 1*b*, each field being dedicated to one pigmentation disorder #k identified on the individual λ; k={1, 2, . . . , K}, K being the number of his or her pigmentation disorders.

Figure 2A:
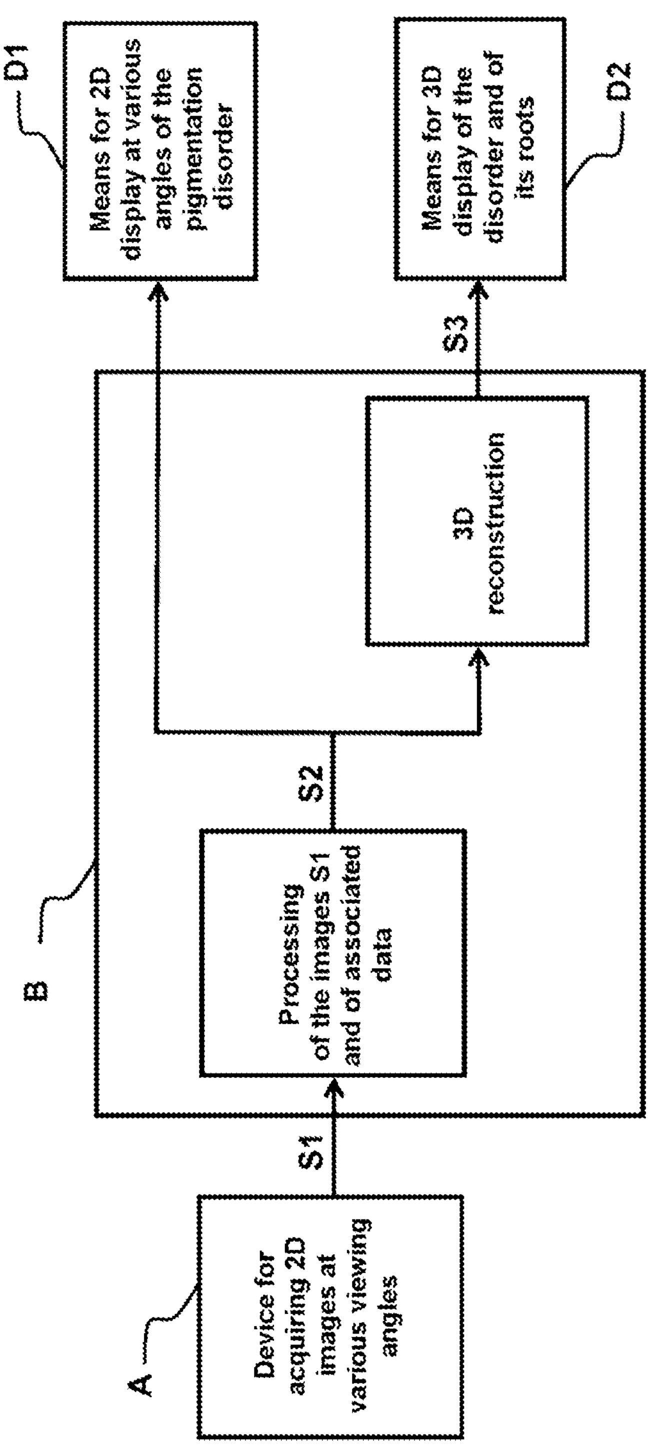
FIG. 2*a* is a schematic representation of a system for imaging a skin pigmentation disorder.
Figure 2B:
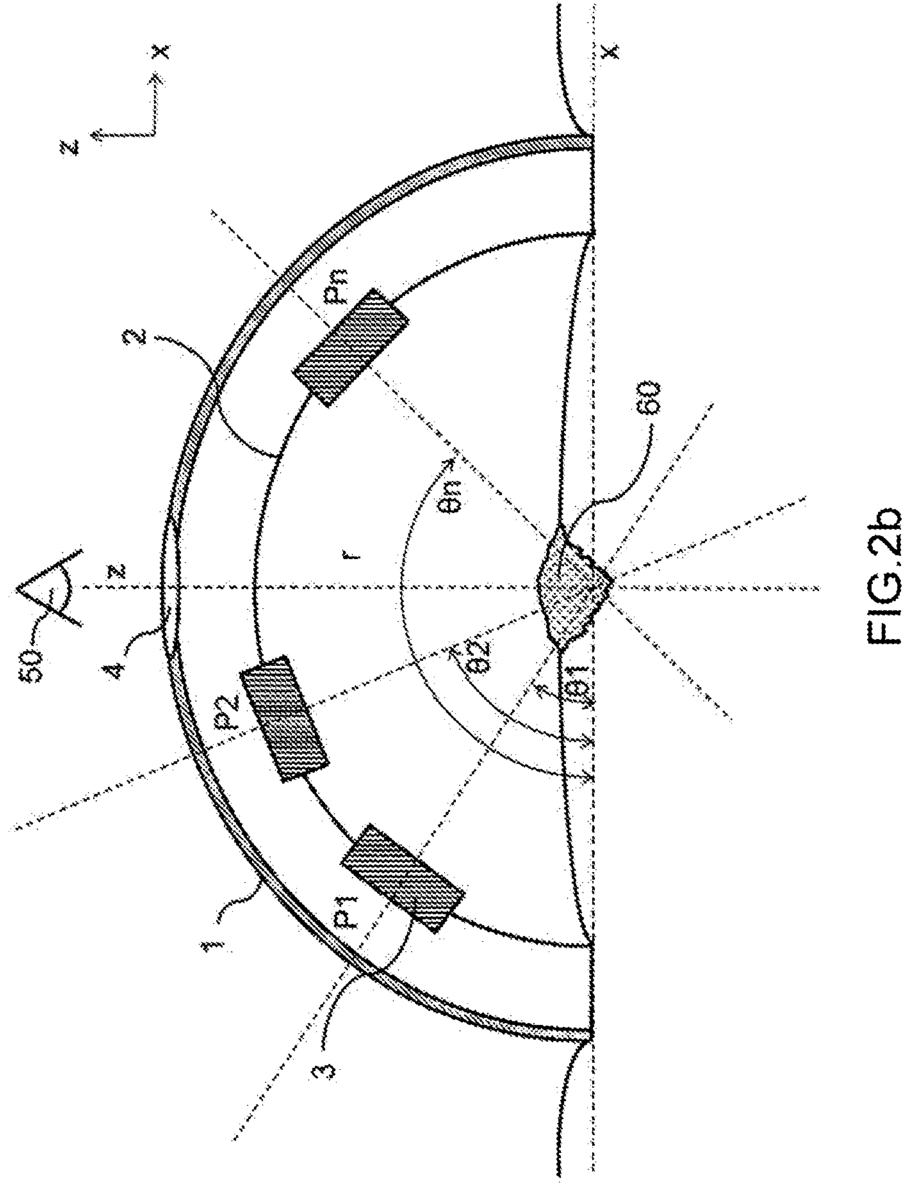
FIG. 2*b* is a schematic representation of an example of a device for acquiring 2D images of this imaging system, in vertical cross section, FIG. 3 schematically shows the content of a first folder Données_2Dθ3D(λ,#k,tkn) containing data related to the pigmentation disorder #k on the date tkn of the individual λ, FIG. 4*a* schematically shows the content of a second folder Données_ParaCalcul(λ,#k,tkn) containing data related to the pigmentation disorder #k on the date tkn of the individual λ, and FIG. 4*b* schematically shows the generation of the first folder Données_2Dθ3D(λ,#k,tkn) and of the second folder Données_ParaCalcul(λ,#k,tkn), FIG. 5 schematically shows the content of a third folder Données_ParaExpertMetier(λ,#k,tkn) containing data related to the pigmentation disorder #k on the date tkn of the individual λ, FIG. 6*a* schematically shows the content of a fourth folder Données_EvoCalclul(λ,#k,tkn) containing data related to the pigmentation disorder #k on the date tkn of the individual λ, FIG. 6*b* schematically shows the generation of this fourth folder Données_EvoCalcul(λ,#k,tkn) of data.

More precisely, the method for characterizing the pigmentation disorders of an individual A comprises the following steps for each pigmentation disorder 60 (or #k):

acquiring 2D images of the pigmentation disorder from a plurality of viewing angles θ, on a date tkm and reconstructing at least one 3D image from these acquired 2D images via an algorithmic method of reflection-tomography type based on an inverse Radon transform. For this image acquisition and reconstruction, a system for imaging a pigmentation disorder, described with reference to FIGS. 2*a* and 2*b*, is preferably used. It comprises a device A for acquiring images, comprising:

at least one emitter of light sources that are optimized in order to allow the wave to penetrate into the epidermis and dermis, this emitter being configured to illuminate said disorder 60, a set of receivers, (this or) these emitters and receivers operating in the visible, infrared (IR) and near IR bands and/or 1st (0.65 μm-0.95 μm) and 2nd (1 μm-1.35 μm) therapeutic windows; the emitter and receiver may be grouped together in an emitter-receiver 3 as shown in FIG. 2*b*, means for positioning the receivers at at least two viewing angles θi so as to obtain at least one image per viewing angle, these receivers being distributed over a spherical cap of radius r; these positioning means may be a rail 2, as shown in FIG. 2*b*, on which are positioned emitter-receivers 3 in fixed positions Pn (or 1 emitter-receiver 3 that slides over the rail 2 in variable Pn positions), a structure 1 for protecting the acquiring device and the operator 50, comprising a window for positioning the receptors so as to direct them toward the pigmentation disorder 60, the structure being intended to be positioned on the skin and having an external surface that is opaque except in the positioning window; the window may be equipped with a magnifying glass 4 as shown in FIG. 2*b*;

as may be seen in FIG. 2*a*, it further comprises:

a unit B for processing the acquired 2D images S1, which further comprises a reflective Radon-transform-based 3D reconstruction module so as to obtain a reconstructed 3D image S3 from the processed 2D images S2, display means that comprise means D1 for displaying the 2D processed images and means D3 for displaying the reconstructed 3D image.

Another 2D and 3D imaging system may of course be used, such as that described in U.S. Pat. No. 8,836,762 "Optronic system and method dedicated to identification for formulating three-dimensional Images" or stereoscopic 3D reconstruction systems.

From these 2D and 3D images, the method comprises the following steps:

storing 2D (acquired) and 3D (reconstructed) images in a first folder "Données_2Dθ3D(λ,#k,tkm)" associated with the individual λ, with the pigmentation disorder #k, with said viewing angles θ and with the date tkm (which is for example the date of the image acquired with the last viewing angle). This first folder, which is shown in FIG. 3, therefore contains:

2D images of the pigmentation disorder #k acquired on the date tkm and at angles θki; i={1, 2, . . . , I}, I being the number of images acquired, and the 3D image(λ,#k,tkm) reconstructed from these 2D images of the pigmentation disorder #k on the date tkm.

Figures 4B, 5:
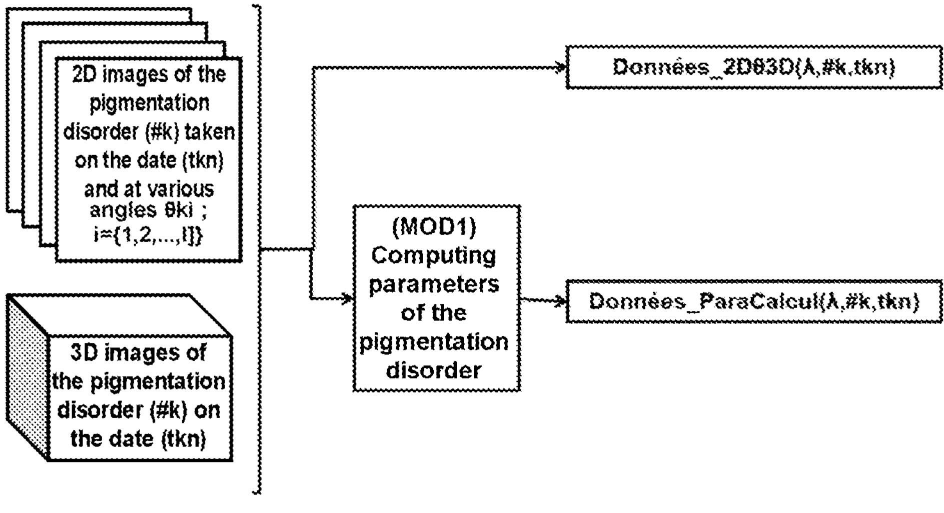

From the 2D and/or 3D images, computing predefined parameters of the pigmentation disorder #k via first computing means MOD1 of the system according to the invention, and storing the parameters in a second folder "Données_ParaCalcul(λ,#k,tkm)", as shown in FIGS. 4*a* and 4*b*, associated with the individual λ, with the pigmentation disorder #k and with the date tkm. The parameters of the second file Données_ParaCalcul(λ,#k,tkn) are for example:

- asymmetry (ParaCalculA): degree of asymmetry of a right-angle view of the pigmentation disorder, the source of which is the 2D image taken at right angles to the pigmentation disorder #k,
- border (ParaCalculB): irregularities (deviations) in the outline of the pigmentation disorder with respect to the average outline computed for the right-angle view, the source of which is the image taken at right angles to the pigmentation disorder #k,
- color (ParaCalculC): colors resulting from chromatic color analysis of the right-angle view, the source of which is the 2D image taken at right angles to the pigmentation disorder #k,
- planar diameter (ParaCalculD): diameter of the circle encompassing the pigmentation disorder in the right-angle view, the source of which is the 2D image taken at right angles to the pigmentation disorder #k,
- 3D isodensity of the pigmentation disorder, allowing a volume delineated by the three-dimensional surface to be obtained, the source of which is the reconstructed 3D image of the pigmentation disorder #k on the date tkn;
- volume diameter: diameter of the sphere encompassing the overall 3D volume of the pigmentation disorder #k,
- thickness of pigmentation disorder #k above the surface of the skin, which is computed in the vertical main cross section of the 3D image of pigmentation disorder #k,
- depth from the surface of the skin of the pigmentation disorder, which is computed in the vertical main cross section of the 3D image of the pigmentation disorder #k,
- number of roots of the pigmentation disorder depthwise from the surface of the skin, the source of which is the 3D image of the pigmentation disorder #k,
- irregularity of the depth of the pigmentation disorder from the surface of the skin, the source of which is the 3D image of the pigmentation disorder #k,
- area covered on the skin by the pigmentation disorder #k, the source of which is the 3D image of the pigmentation disorder #k,
- volume in $\mu m^3$, of the voxels contained in the 3D isodensity of the pigmentation disorder.

The user may define his or her own analysis cross section in the 3D image of the pigmentation disorder with a view to extracting his or her own parameters of interest.

Getting an expert to evaluate computed parameters and storing the evaluated parameters in an associated third folder "Données_ParaExpert(λ,#k,tkm)", shown in FIG. 5. The expert who evaluates these parameters is a doctor or a system-expert recognized in the field.

Iterating at least one of the previous four steps on a plurality of dates tkm up to tkn (tkn>tkm); at least one of the three folders (first, second and third) is thus obtained as many times as there are iterations. Generally the four steps are iterated and three new folders are then obtained.

Figure 6B:
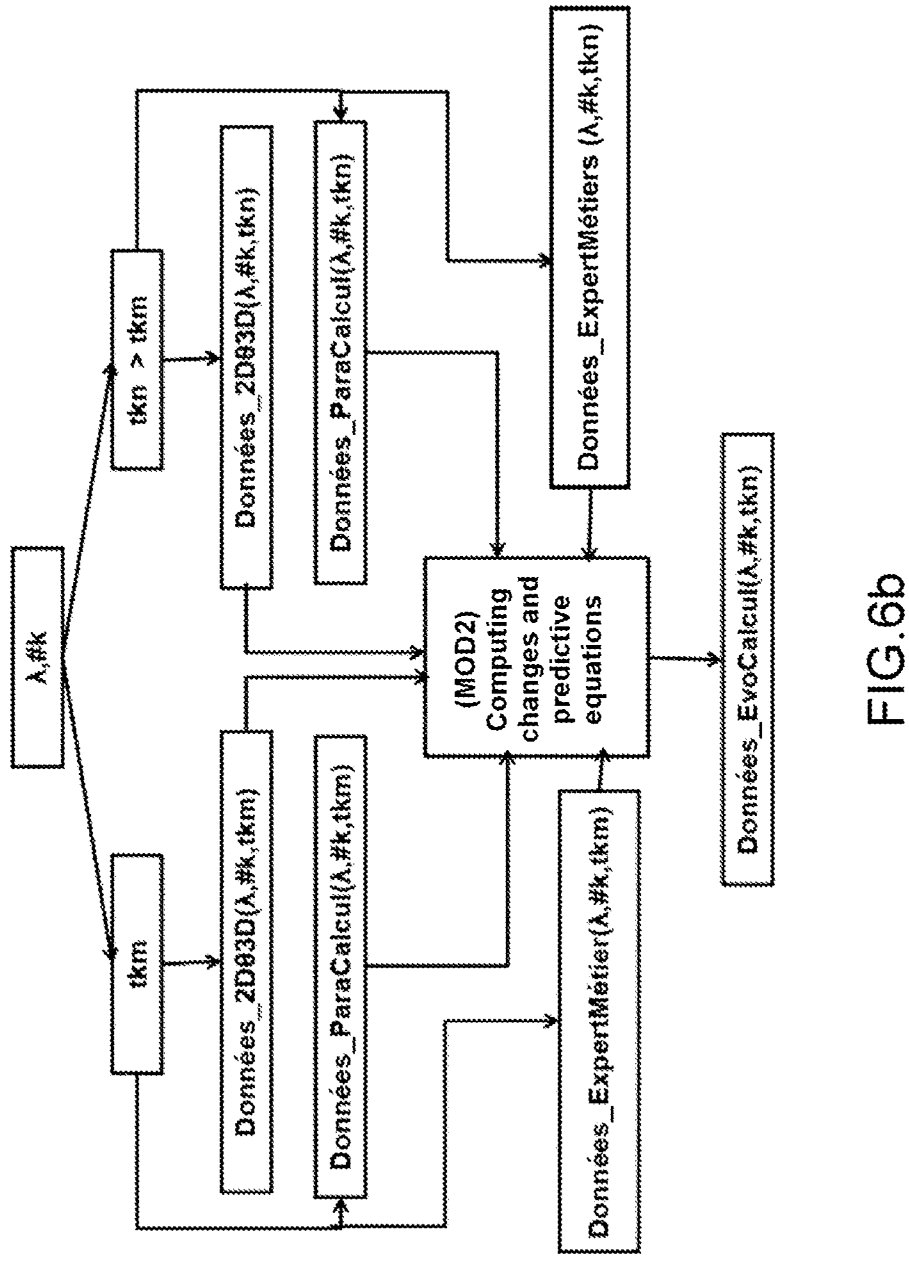

For each iteration, comparing the data of the first, second and third folders in at least one period between the dates tkn and tkm and identifying changes in these data (2D, 3D images, parameters such as various present parameters, asymmetry, border, color, etc.) in the first, second and third folders via second computing means MOD2 of the system according to the invention, and storing the changes in said data in a fourth folder "Données_EvoCalcul(λ,#k,tkn)" as shown in FIGS. 6*a* and 6*b*.

The means MOD2 for computing the comparisons and identifying changes in the pigmentation disorders for example allow the user (non-doctor operator or doctor) to:

- compare, by virtue of the 3D image, the dimensions of the areas and irregularities in the surfaces and in the volumes of the pigmentation disorder #k on the dates tkm and tkn;
- compare the following computed parameters: asymmetries, borders, colors, (planar and volume) diameters, thicknesses above the skin, depths from the surface of the skin, the numbers of depthwise roots from the surface of the skin, irregularities in the thickness of the depth and the areas covered on the skin of the pigmentation disorder #k, on the dates tkm and tkn;
- compare the parameters A, B, C and D evaluated by the expert in the field for the same pigmentation disorder #k on the dates tkm and tkn;
- define other particular comparative elements of the same pigmentation disorder #k on the different dates tkm and tkn, such as, for example, comparison of 2D images taken at the same viewing angle or comparison of cross sections in 3D volumes or any other particular comparative element.

The identification of the progression is for example: "no change" or "positive progression", or etc.

Figures 7, 8:
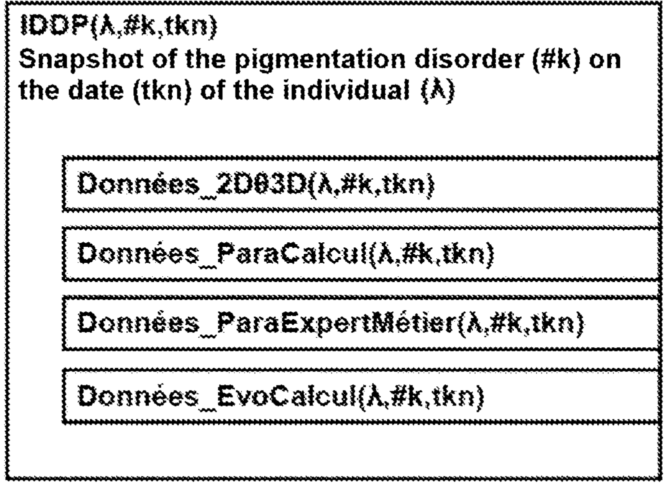
FIG. 7 is a schematic representation of the content of a fifth folder corresponding to a snapshot IDDP(λ,#k,tkn) of the pigmentation disorder for pigmentation disorder #k on the date tkn of the individual λ.
FIG. 8 is a schematic representation of the content of a sixth folder corresponding to the dynamic profile PDDP(λ, #k) of the pigmentation disorder for pigmentation disorder #k of the individual λ.

Then grouping the four folders associated with tkn into a fifth folder "IDDP(λ,#k,tkn)" representing a snapshot of the pigmentation disorder #k of the individual A on the date tkn, as shown in FIG. 7.

The computing means MOD2 are interactive, i.e. the user (non-doctor operator, or doctor) may interact with them, allowing him or her to create, for the same pigmentation disorder #k, various fourth folders according to the period of progression chosen between tkm and tkn (full or partial period). Specifically, the comparison of the same pigmentation disorder #k, between the dates tkm and tkn, may be based on:

1. a unitary incremental change if n=m+1, and/or
2. any change if n>m+1, and/or
3. an overall change if n corresponds to the last date and m to the first date of the pigmentation disorder.

As a result, there are therefore at least as many fifth instantaneous folders "IDDP(λ,#k,tkn)" as there are, on the one hand, iterations and, on the other hand, various periods of progression between tkn and tkm.

Thus for an individual A and for a pigmentation disorder #k, the situations that are possible with respect to a snapshot IDDP(λ,#k,tkn) of the pigmentation disorder, on the date tkn, may be:

Partial situation 1: 2D images and 3D images taken on the date tkn; in this case, the first folder Data_2Dθ3D(λ, #k,tkn) is generated automatically, and the second folder Données_ParaCalcul(λ,#k,tkn) is generated by the means MOD1 for computing the parameters of the pigmentation disorder. The computing means MOD2 allow the third folder Données_EvoCalcul(λ,#k,tkn) to be generated if there is at least one previous folder Données_EvoCalcul(λ,#k,tkm).

Partial situation 2: no 2D images and no 3D images taken on the date tkn; therefore the folder Données_2Dθ3D (λ,#k,tkn) is empty as is the 2nd folder Données_ParaCalcul(λ,#k,tkn); however, if pigmentation disorder #k is evaluated by the expert in the field on this date tkn, then the third folder Données_ParaExpertMetier (λ,#k,tkn) is generated and the module MOD2 in turn generates the fourth folder Données_EvoCalcul(λ,#k, tkn) if there is at least one previous third folder Données_ParaExpertMetier(λ,#k,tkm);

Complete situation: 2D images and 3D images taken on date tkn and evaluation made by the expert in the field on this date tkn; in this case all four folders Données_2Dθ3D(λ,#k,tkn),Données_ParaCalcul(λ,#k, tkn), Données_ParaExpertMetier(λ,#k,tkn) and Données_EvoCalcul(λ,#k,tkn) are generated.

Other equivalent situations are also possible.

These IDDP(λ,#k,tkn) are aggregated into a sixth folder "PDDP(λ,#k)" which represents a dynamic profile of the pigmentation disorder #k of the individual λ, as shown in FIG. 8.

The previous steps are reiterated for each other pigmentation disorder of the individual. A dynamic profile of the pigmentation disorder of the individual A is then obtained for each other pigmentation disorder.

It is then possible to generate, for the individual λ, a knowledge base "BCDP(λ)" of his or her pigmentation disorders, aggregating the sixth folders, i.e. his or her dynamic profiles for each pigmentation disorder, as already shown in FIG. 1*b*. One of the advantages of this BCDP(λ) base with respect to conventional bases is that it is possible to see inside the pigmentation disorder through the 3D image of the pigmentation disorder via slices or representations of MIP type (MIP being the acronym of maximum intensity projection) and that may allow the expert to quantify the progressive behavior of the pigmentation disorder using a set of predictive equations established from the global knowledge base of pigmentation disorders that is defined below.

Figure 9:
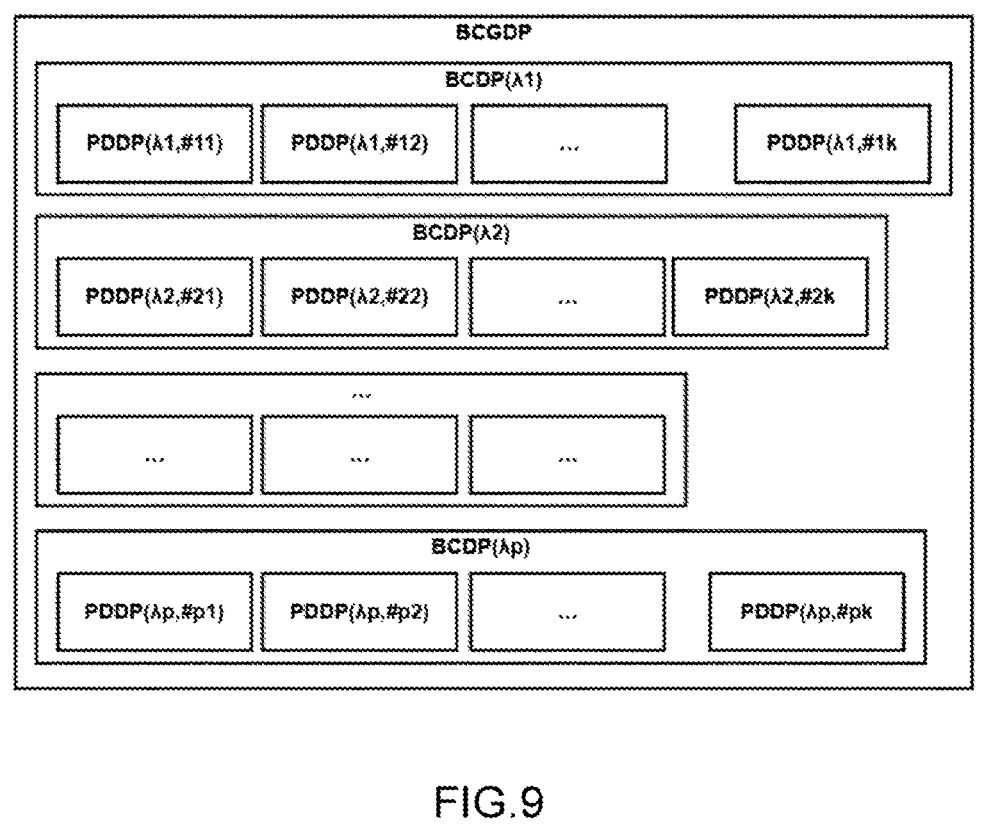

A global knowledge base (BCGDP) of pigmentation disorders may be created by aggregating the knowledge bases BCDP(λ) of the pigmentation disorders of a plurality of individuals {λ1, λ2, . . . , λp}, p being the number of individuals in the base, as already shown in FIG. 9.

By way of non-limiting example, the aggregation of knowledge of pigmentation disorders of a plurality of individuals into a global knowledge base of pigmentation disorders is linked to a selection criterion such as: age group, sex, geographical location, etc.

This global knowledge base of pigmentation disorders contributes to global statistical analyses, to the establishment of predictive equations (based on representative descriptors obtained from univariate analyses of the Kaplan-Meier type and multivariate analyses of Cox-model type) on the basis of two- or three-dimensional parameters of change, and of roughness parameters for example, and may also be used as input bases with a view to carrying out automatic evaluations using advanced technologies such as deep learning for example.

The method according to the invention mainly applies to the biomedical field, for early identification of cutaneous or sub-cutaneous disorders.

Another example of an application is orthodontics, which requires internal change in the gum line and of root canals to be monitored.

The invention claimed is:

1. A method for characterizing skin pigmentation disorders of an individual, which comprises the following steps:

for each pigmentation disorder:

on a first date:

acquiring 2D images of a pigmentation disorder on said first date and from a plurality of viewing angles with a device for acquiring images and reconstructing at least one 3D image from processed 2D images with a reconstruction processing unit, wherein the reconstructing the at least one 3D image from the processed 2D images with the reconstruction processing unit comprises reconstructing the at least one 3D image from the processed 2D images with reflection-tomography based on an inverse Radon transform, and wherein the reconstructing the at least one 3D image from the processed 2D images with the reconstruction processing unit comprises reconstructing the at least one 3D image from the processed 2D images with an optronic system configured and/or operable for identification and formulating three-dimensional Images or a stereoscopic 3D reconstruction system, storing said 2D images and 3D images in a first folder associated with the individual, with the pigmentation disorder and with said first date, computing from said 2D images and 3D images, predefined parameters of the pigmentation disorder via a first computing module having a processor, and storing said parameters in a second folder associated with the individual, with the pigmentation disorder and with said first date, and requesting an expert to evaluate said parameters, receiving an evaluation from the expert, and storing the evaluation in a third folder associated with the individual, with the pigmentation disorder and with said first date, iterating at least one of the previous four steps on a plurality of subsequent dates which are subsequent to said first date, and for each iteration:

comparing, with a display device data of the first, second and third folders in at least one period between the first date and the subsequent dates and identifying changes in said data with a second computing module having a processor, the comparison of the same individual's pigmentation disorder, between the first date and the subsequent dates, being based on a user interaction which comprises selecting one among the subsequent dates, and further based on any change if the first date and the one among the subsequent dates are not immediately consecutive, storing the changes in at least one fourth folder, associated with the individual, with the pigmentation disorder and with said first date, with one fourth folder per period, for each fourth folder, grouping the first, second, third and fourth folders associated with said first date into a fifth folder with the individual, with the pigmentation disorder and with said first date, defining a snapshot of the pigmentation disorder, and aggregating the fifth folders into a sixth folder with the individual and with the pigmentation disorder, defining a dynamic profile of the pigmentation disorder, iterating the previous steps to obtain a sixth folder for each other pigmentation disorder of the individual, and generating, for the individual, a knowledge base of his or her pigmentation disorders by aggregating the sixth folders, wherein the method provides identification of a progression of skin pigmentation disorders of the individual.

2. The method for characterizing skin pigmentation disorders of an individual as claimed in claim 1, wherein the parameters are computed by the first computing module from the 2D images and the parameters are at least an asymmetry, a border, a color, and a diameter.

3. The method for characterizing skin pigmentation disorders of an individual as claimed in claim 1, wherein the parameters are computed by the first computing module from reconstructed 3D images and the parameters comprise a 3D isodensity, a volume diameter, a thickness above a surface of the skin, a depth, a number of roots, an irregularity of the depth, an area on the skin, and a volume of voxels contained in the 3D isodensity.

4. A system for characterizing skin pigmentation disorders of an individual, comprising a processor programmed to implement the following steps:

for each pigmentation disorder:

on a first date:

acquiring 2D images of a pigmentation disorder on said first date and from a plurality of viewing angles with a device for acquiring images and reconstructing at least one 3D image from processed 2D images with a reconstruction processing unit, wherein the reconstructing the at least one 3D image from the processed 2D images with the reconstruction processing unit comprises reconstructing the at least one 3D image from the processed 2D images with reflection-tomography based on an inverse Radon transform, and wherein the reconstructing the at least one 3D image from the processed 2D images with the reconstruction processing unit comprises reconstructing the at least one 3D image from the processed 2D images with an optronic system configured and/or operable for identification and formulating three-dimensional Images or a stereoscopic 3D reconstruction system storing said 2D images and 3D images in a first folder associated with the individual, with the pigmentation disorder and with said first date, computing from said 2D images and 3D images, predefined parameters of the pigmentation disorder via a first computing module of the system, and storing said parameters in a second folder associated with the individual, with the pigmentation disorder and with said first date, and acquiring an evaluation of said parameters and storing said evaluation in a third folder associated with the individual, with the pigmentation disorder and with said first date, iterating at least one of the previous four steps on a plurality of subsequent dates which are subsequent to said first date, and for each iteration:

comparing data of the first, second and third folders in at least one period between the first date and the subsequent dates and identifying changes in said data with a second computing module of the system, the comparison of the same individual's pigmentation disorder, between the first date and the subsequent dates, being based on a user interaction which comprises selecting one among the subsequent dates, and further based on any change if the first date and the one among the subsequent dates are not immediately consecutive, storing the changes in at least one fourth folder associated with the individual, with the pigmentation disorder and with said first date, with one fourth folder per period, for each fourth folder, grouping the first, second, third and fourth folders associated with said first date into a fifth folder with the individual, with the pigmentation disorder and said first date, defining a snapshot of the pigmentation disorder, and aggregating the fifth folders into a sixth folder with the individual and with the pigmentation disorder, defining a dynamic profile of the pigmentation disorder, iterating the previous steps to obtain a sixth folder for each other pigmentation disorder of the individual, and generating, for the individual, a knowledge base of his or her pigmentation disorders by aggregating the sixth folders, wherein the system is configured to identify a progression of skin pigmentation disorders of the individual.

5. The system for characterizing skin pigmentation disorders of an individual as claimed in claim 4, wherein the parameters are computed by the first computing module from the 2D images and the parameters are at least an asymmetry, a border, a color, and a diameter.

6. The system for characterizing skin pigmentation disorders of an individual as claimed in claim 4, wherein the parameters are computed by the first computing module from reconstructed 3D images and the parameters comprise a 3D isodensity, a volume diameter, a thickness above a surface of the skin, a depth, a number of roots, an irregularity of the depth, an area on the skin, and a volume of voxels contained in the 3D isodensity.

7. The method for characterizing skin pigmentation disorders of an individual as claimed in claim 1, further comprising:

configuring the device for acquiring images with at least one emitter of light sources that are optimized in order to allow a light wave to penetrate into an epidermis and a dermis;

configuring the device for acquiring images with a set of receivers configured to operate in a visible band, an infrared (IR) band, and/or a near IR band;

configuring the device for acquiring images with a device to position the set of receivers in at least two viewing angles; and obtaining at least one image per viewing angle with the set of receivers.

8. The method for characterizing skin pigmentation disorders of an individual as claimed in claim 1, further comprising:

configuring a display device to display 2D processed images; and configuring the display device to display a reconstructed 3D image.

9. The system for characterizing skin pigmentation disorders of an individual as claimed in claim 4, wherein the device for acquiring images is configured with at least one emitter of light sources that is configured to be optimized in order to allow a light wave to penetrate into an epidermis and a dermis;

wherein the device for acquiring images is configured with a set of receivers configured to operate in a visible band, an infrared (IR) band, and/or a near IR band; and wherein the device for acquiring images is configured with a device configured to position the set of receivers in at least two viewing angles so as to obtain at least one image per viewing angle.

10. The system for characterizing skin pigmentation disorders of an individual as claimed in claim 4, further comprising a display device to display 2D processed images and/or display a reconstructed 3D image.

11. The method for characterizing skin pigmentation disorders of an individual as claimed in claim 1, further comprising automatically generating data for the folders that comprise the 2D images and 3D images.

12. The system for characterizing skin pigmentation disorders of an individual as claimed in claim 4 being configured and/or operable to automatically generate data for the folders that comprise the 2D images and 3D images.

13. The system for characterizing skin pigmentation disorders of an individual as claimed in claim 4, wherein the reconstruction processing unit is configured and/or operable for reconstructing the at least one 3D image from the processed 2D images with reflection-tomography based on an inverse Radon transform.

14. The system for characterizing skin pigmentation disorders of an individual as claimed in claim 4, wherein the reconstruction processing unit is configured and/or operable for reconstructing the at least one 3D image from the processed 2D images with an optronic system configured and/or operable for identification and formulating three-dimensional Images or a stereoscopic 3D reconstruction system.

15. A system for imaging a pigmentation disorder and characterizing skin pigmentation disorders of an individual, comprising a processor programmed to implement the system being configured and/or operable to implement following steps:

for each pigmentation disorder:

on a first date:

acquiring 2D images of a pigmentation disorder on said first date and from a plurality of viewing angles with a device for acquiring images and reconstructing at least one 3D image from processed 2D images with a reconstruction processing unit, wherein the reconstructing the at least one 3D image from the processed 2D images with the reconstruction processing unit comprises reconstructing the at least one 3D image from the processed 2D images with reflection-tomography based on an inverse Radon transform, and wherein the reconstructing the at least one 3D image from the processed 2D images with the reconstruction processing unit comprises reconstructing the at least one 3D image from the processed 2D images with an optronic system configured and/or operable for identification and formulating three-dimensional Images or a stereoscopic 3D reconstruction system, storing said 2D images and 3D images in a first folder associated with the individual, with the pigmentation disorder and with said first date, computing from said 2D images and 3D images, predefined parameters of the pigmentation disorder via a first computing module of the system, and storing said parameters in a second folder associated with the individual, with the pigmentation disorder and with said first date, and acquiring an evaluation of said parameters and storing said evaluation in a third folder associated with the individual, with the pigmentation disorder and with said first date, iterating at least one of the previous four steps on a plurality of subsequent dates which are subsequent to said first date, and for each iteration:

comparing data of the first, second and third folders in at least one period between the first date and the subsequent dates with a second computing module, identifying changes in said data with the second computing module of the system, the comparison of the same individual's pigmentation disorder, between the first date and the subsequent dates, being based on a user interaction which comprises selecting one among the subsequent dates, and further based on any change if the first date and the one among the subsequent dates are not immediately consecutive, storing the changes in at least one fourth folder associated with the individual, with the pigmentation disorder and with said first date, with one fourth folder per period, for each fourth folder, grouping the first, second, third and fourth folders associated with said first date into a fifth folder with the individual, with the pigmentation disorder and said first date, defining a snapshot of the pigmentation disorder, and aggregating the fifth folders into a sixth folder with the individual and with the pigmentation disorder, defining a dynamic profile of the pigmentation disorder, iterating the previous steps to obtain a sixth folder for each other pigmentation disorder of the individual, and generating, for the individual, a knowledge base of his or her pigmentation disorders by aggregating the sixth folders, wherein the system is configured to identify a progression of skin pigmentation disorders of the individual;

wherein the system is configured and/or operable to automatically generate data for the folders that comprise the 2D images and 3D images;

wherein the device for acquiring images is configured with at least one emitter of light sources that is configured to be optimized in order to allow a light wave to penetrate into an epidermis and a dermis;

wherein the device for acquiring images is configured with a set of receivers configured to operate in a visible band, an infrared (IR) band, and/or a near IR band; and wherein the device for acquiring images is configured with a device configured to position the set of receivers in at least two viewing angles so as to obtain at least one image per viewing angle.

* * * * *